United States Patent
Brunzel et al.

(10) Patent No.: US 11,021,426 B2
(45) Date of Patent: Jun. 1, 2021

(54) METHOD FOR SYNTHESISING AN UNSATURATED MACROCYCLIC KETONE

(71) Applicant: Symrise AG, Holzminden (DE)

(72) Inventors: Tom Brunzel, Rostock (DE); Angela Köckritz, Berlin (DE); Andreas Martin, Berlin (DE); Diego A. Jaime Trevino, Holzminden (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/758,630

(22) PCT Filed: Oct. 25, 2017

(86) PCT No.: PCT/EP2017/077298
§ 371 (c)(1),
(2) Date: Apr. 23, 2020

(87) PCT Pub. No.: WO2019/081009
PCT Pub. Date: May 2, 2019

(65) Prior Publication Data
US 2020/0347002 A1  Nov. 5, 2020

(51) Int. Cl.
| | | |
|---|---|---|
| *C07C 45/34* | (2006.01) | |
| *B01J 23/00* | (2006.01) | |
| *B01J 31/00* | (2006.01) | |
| *B01J 23/44* | (2006.01) | |
| *B01J 31/22* | (2006.01) | |
| *C07C 49/587* | (2006.01) | |

(52) U.S. Cl.
CPC .............. *C07C 45/34* (2013.01); *B01J 23/44* (2013.01); *B01J 31/2226* (2013.01); *C07C 49/587* (2013.01); *C07C 2601/18* (2017.05)

(58) Field of Classification Search
CPC ........ C07C 45/34; B01J 23/44; B01J 31/2226
See application file for complete search history.

(56) References Cited

U.S. PATENT DOCUMENTS 8,507,728 B2 * 8/2013 Kaneda ................. C07C 45/34
568/360
2014/0194604 A1  7/2014 Morandi et al.

FOREIGN PATENT DOCUMENTS

EP  2364965 A1  9/2011

OTHER PUBLICATIONS

Villemin et al., "Supported Metalated Phthalocyanine as Catalyst for Oxidation by Molecular Oxygen. Synthesis of Quinones and Carbonyl Compounds," Synthetic Communications 32(10): 1501-1515 (Jan. 1, 2002).
Deluca et al., "Wacker-Type Oxidation of Internal Alkenes using Pd(Quinox) and TBHP," Journal of Organic Chemistry 78(4): 1682-1686 (Feb. 2013).

* cited by examiner

*Primary Examiner* — Sikarl A Witherspoon
(74) *Attorney, Agent, or Firm* — Dilworth & Barrese, LLP

(57) ABSTRACT

A method for producing unsaturated macrocyclic monoketones comprising the following steps: (a) preparing macrocyclic dienes with a ring size of at least 9 carbon atoms; (b) contacting the starting materials from step (a) with (b1) a palladium(II) salt and/or a palladium(II) complex; and (b2) an oxidant; and (b3) a solvent; and optionally (b4) a ligand; and optionally (b5) a co-catalyst; and optionally (b6) an acid.

16 Claims, 2 Drawing Sheets

METHOD FOR SYNTHESISING AN UNSATURATED MACROCYCLIC KETONE

FIELD OF THE INVENTION

Figure 1:
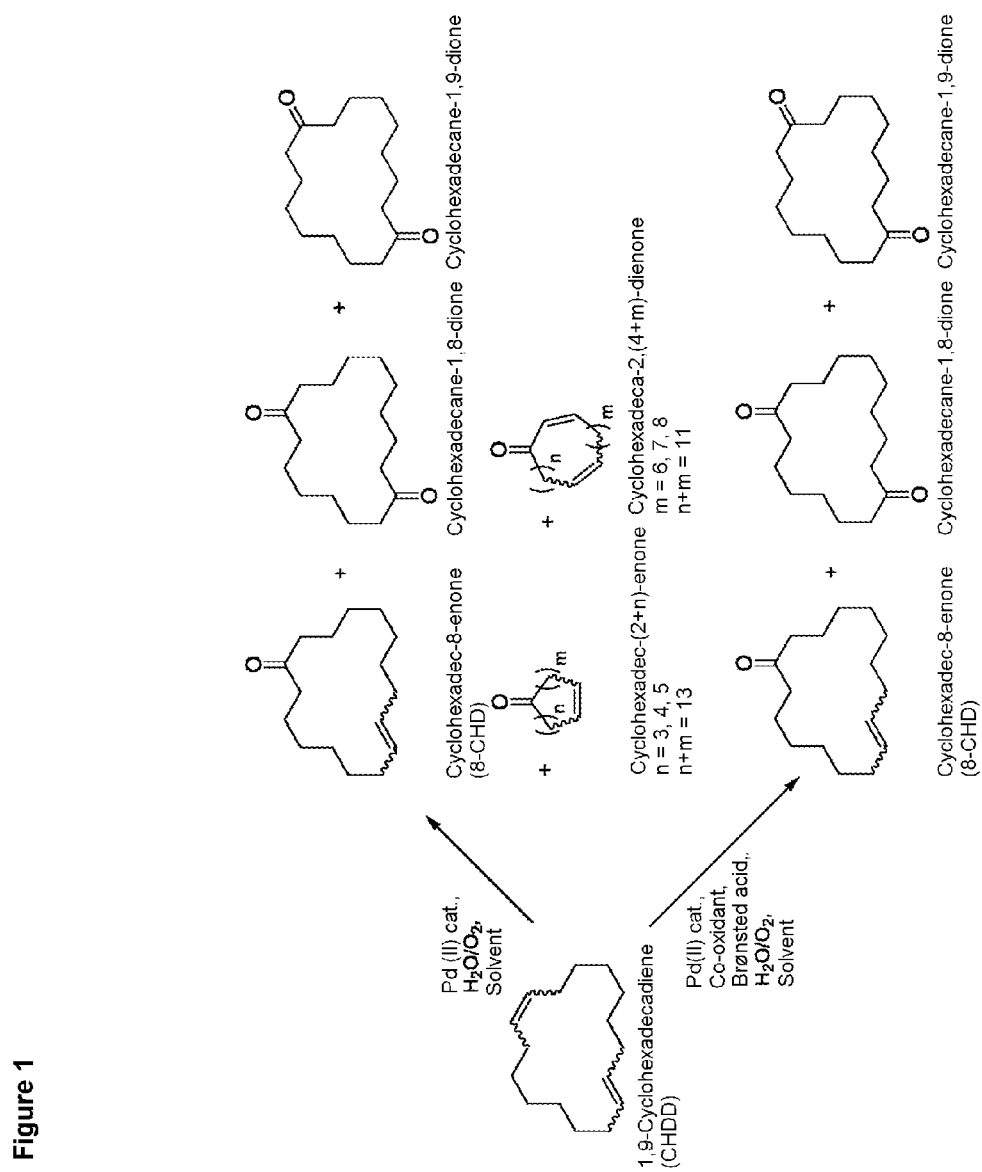

The field of the invention is the preparation of unsaturated macrocyclic monoketones from a macrocyclic diene in a one-step oxidation in the presence of an oxidant, a palladium (II) salt and/or a palladium(II) complex, and a solvent.

STATE OF THE ART

Ketones are suitable as solvents and chemical raw materials and are accordingly used in various areas. Such ketones are generally prepared by two-step reaction methods in which an alcohol generated by hydration of an olefin is dehydrated. Nowadays, simpler methods are known, including one-step reaction methods in which an olefin is oxidized directly.

Two-step methods for preparing macrocyclic monoketones are known from the prior art. The industrial synthesis of macrocyclic ketones is, for example, achieved by a selective monoepoxidation and rearrangement of the epoxide to the ketone in the presence of alkali metal halides or alkaline earth metal halides, as described in B. D. Mookherjee, R. W. Trenkle, R. R. Patel, *J. Org. Chem.* 36 (1971), 3266. A reduction of the epoxy group to a hydroxy group, followed by subsequent oxidation to the ketone is described, for example, in U.S. Pat. No. 3,718,696.

The Wacker process using a $PdCl_2/CuCl_2$ catalyst is known as one of the methods for the direct oxidation of an olefin. This method is effective for the oxidation of terminal olefins having a carbon-carbon double bond (hereinafter abbreviated as "C=C bond") at one end of a molecule thereof. However, this process achieves only low reactivity when used for the oxidation of internal olefins having a C=C bond in a non-terminal position. This method likewise does not achieve satisfactory results when the number of carbon atoms in the starting material is increased, because the rate of reaction is appreciably reduced. For this reason, the use of the Wacker process in industry is restricted to the production only of lower carbonyl compounds such as acetaldehyde and acetone that are obtained through oxidation of lower terminal olefins.

Kaneda et al. developed a method that does not require a co-oxidant for the reoxidation of Pd(0), but in which oxygen brings about direct oxidization of Pd(0) to Pd(II). This is done using a dimethylacetamide/$H_2O$ mixture at 80° C. (T. Mitsudome, T. Umetani, N. Nosaka, K. Mori, T. Mizugaki, K. Ebitani, K. Kaneda, *Angew. Chem. Int. Ed.* 45 (2006) 481). This method also allows the oxidation of linear internal olefins and cyclic olefins such as cyclohexene (T. Mitsudome, K. Mizumoto, T. Mizugaki, K. Jitsukawa, K. Kaneda, *Angew. Chem. Int. Ed.* 49 (2010) 1238). The methodology was, however, successful only when chlorine-containing palladium catalysts were used. Our own investigations have shown that this method affords only insufficient yields of the desired ketones from macrocyclic olefins and dienes as substrates, even when a co-oxidant is used.

A further variant of the Wacker oxidation of olefins using cationic palladium complexes is described in US 20140194604. However, no macrocyclic dienes are used as the starting substrate here.

Similarly, WO 2010/061807 describes a modified version of the Wacker process that includes the use of macrocyclic dienes as the starting substrate. However, only dienes having a maximum ring size of 8 carbon atoms are described here.

Macrocyclic dienes form a chelate complex with Pd(II) species/compounds. The further coordination of the reacting components is, however, hindered by the spatial arrangement of the ligand and the flexibility thereof, which limits the activity and selectivity of the reaction considerably. This is one of the reasons why such macrocyclic dienes react only very poorly in the methods known from the prior art. This is reinforced further by the fact that these very nonpolar macrocyclic dienes have only limited solubility in polar solvents. Satisfactory yields accordingly cannot be obtained using the methods known from the prior art.

The object of the present invention was therefore to provide methods that overcome the disadvantages of the prior art. To be precise, the object was to provide a method that allows simple process control that is economical with materials and energy and thus sustainable and at the same time allows commercial yields to be achieved.

DESCRIPTION OF THE INVENTION

This object is achieved by the subject of the present invention, which relates to a method for preparing unsaturated macrocyclic monoketones comprising the following steps
(a) providing macrocyclic dienes having a ring size of at least 9 carbon atoms;
(b) contacting the starting materials from step (a) with
    (b1) a palladium(II) salt and/or a palladium(II) complex; and
    (b2) an oxidant; and
    (b3) a solvent; and optionally
    (b4) a ligand; and optionally
    (b5) a co-catalyst; and optionally
    (b6) an acid.

It was surprisingly found that unsaturated macrocyclic monoketones may be prepared in considerably higher yields by the above-mentioned method. Commercial use of the resulting isomers is likewise possible, which makes the method extremely sustainable and efficient.

A further advantage of the invention is that the macrocyclic dienes react so effectively with the method of the invention that, even when the macrocyclic dienes are present as a mixture of E,E, E,Z and Z,Z isomers, which each have different reactivity, it is possible for them to be selectively oxidized to a monoketone without the formation of undesirable amounts of diketones.

FIG. 1 illustrates an example of the sequence of events of the preparative method according to the invention. This figure is, however, only an example and is not intended to be limiting in any way.

The macrocyclic diene (a) preferably contains two non-conjugated double bonds. In a preferred embodiment of the invention, the macrocyclic diene has a ring size of 9 to 30 carbon atoms, preferably 12 to 18 carbon atoms, and more preferably 16 carbon atoms. In a particularly preferred embodiment, the macrocyclic diene (a) is 1,9-cyclohexadecadiene (CHDD).

In a further preferred embodiment of the method according to the invention, the macrocyclic diene (a) used is a mixture of different stereoisomers. In a particularly preferred embodiment of the method according to the invention, the macrocyclic diene (a) is 1,9-cyclohexadecadiene (CHDD) and is present as a mixture of E,E, E,Z and Z,Z isomers.

Preference is given to the preparation of cyclohexadec-8-enone (8-CHD) by the preparative method of the invention. In a particularly preferred embodiment of the invention, CHHD is used as the macrocyclic diene (a), wherein 8-CHD is obtained using the preparative method of the invention.

In a first embodiment of the invention, the solvent (b3) is a polar aprotic solvent. The solvent (b3) is preferably selected from the group consisting of N,N-disubstituted open-chain and cyclic acid amides, for example dimethylformamide, dimethylacetamide, diethylacetamide, dimethylpropionamide, N-methylpyrrolidone, aliphatic, cycloaliphatic or aromatic nitriles such as acetonitrile, propionitrile or benzonitrile, or linear and cyclic ethers, cyclic lactones and carbonates.

In a first embodiment of the invention, small amounts of water are preferably added to the solvent (b3). This is preferably in an amount of 0.1% to 25% by volume, more preferably in an amount of 1-20% by volume, and particularly preferably in an amount of 5-15% by volume. The volume percentages are based here on the solvent (b3).

In a first embodiment of the invention, the presence of the ligand (b4) is additionally mandatory in the method according to the invention. The ligand is preferably a bidentate ligand. The use of a bidentate ligand is consequently advantageous because, on the one hand, it possesses donor properties strong enough to provide molecular stabilization of the palladium(II) salt and/or palladium(II) complex and is thus able to prevent palladium(0) from precipitating. On the other hand, the ligand may have bulky substituents that prevent chelation of palladium by the starting material (a). The ligand preferably contains N,N, N,O, N,S, and/or O,O donor atoms. More preferably, the ligand contains N,N, N,O, and/or O,O donor atoms. These atoms may be part of a cyclic system or may be connected to one another via other suitable bridging groups.

Figure 2:
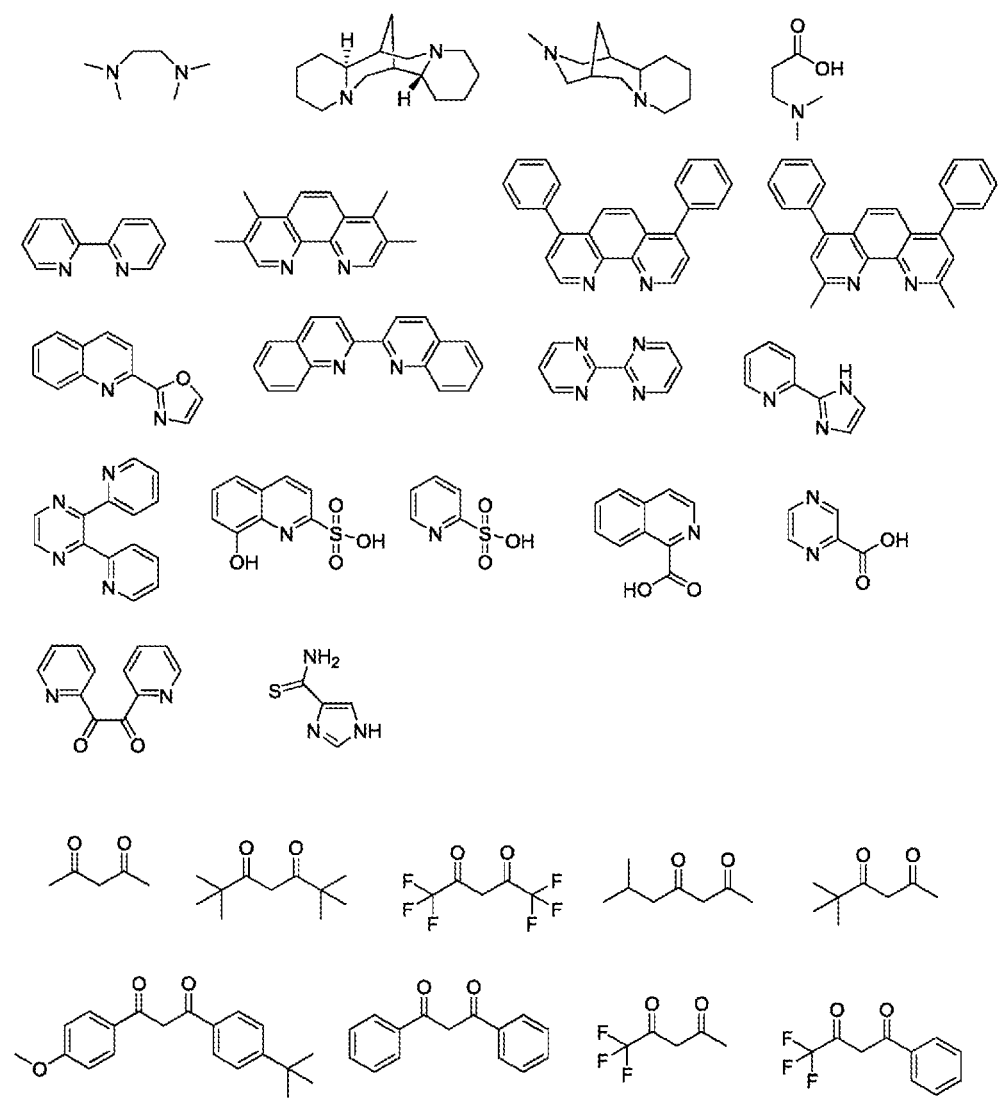

FIG. 2 illustrates bidentate ligands used for one embodiment of the method according to the invention. This figure is shown by way of example and is not intended to be limiting.

In a first embodiment of the method according to the invention, the palladium(II) salt and/or the palladium(II) complex (b1) are selected from the group consisting of palladium chloride, palladium bromide, $H_2PdCl_4$, $Li_2PdCl_4$, $Na_2PdCl_4$, $K_2PdCl_4$, $(NH_4)_2PdCl_4$, palladium acetate, palladium trifluoroacetate, palladium benzoate, tetrakis(acetonitrile)palladium(II) tetrafluoroborate, tetrakis(acetonitrile)palladium(II) bis(trifluoromethanesulfonate), palladium nitrate, and/or palladium sulfate.

A first embodiment of the method according to the invention is additionally characterized in that the palladium (II) salt and/or the palladium(II) complex (b1) form with the bidentate ligand (b4) a palladium compound of the formula (I) and/or of the formula (II)

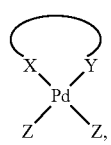

I where X and Y each independently represent N,N, O,N or O,O; and
where Z each independently represent a halogen, acetate, trimethylacetate, trifluoromethylacetate, MeCN, PhCN, $NO_2$, NO, nitrate, nitrite or sulfate;

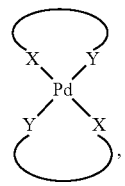

II where X and Y each independently represent O,O, N,N or O,N.

In a first embodiment of the invention, the palladium compound thus obtained is in a concentration from 0.01 to 25 mol %, preferably from 1 to 20 mol %, more preferably from 1 to 15 mol %, and particularly preferably from 1 to 5 mol %. The mol % values are in each case based on the starting material (a).

In a first embodiment of the invention, the palladium compound is preferably a neutral palladium catalyst.

The formation of the palladium compounds of the formulas (I) and/or (II) may occur either in situ or in a separate preparation process ex situ. In the case of separate ex-situ preparation, instead of the palladium(II) salt and/or palladium(II) complex (b) and the ligands (b4), the palladium compounds are contacted directly with the starting material (a) of the preparative method according to the invention.

In a first embodiment of the invention, an oxygen-containing gas is used as the oxidant (b2). The oxygen-containing gas preferably contains oxygen in a concentration from 1% to 100% by volume, more preferably from 5% to 100% by volume, and most preferably from 21% to 100% by volume.

In a first embodiment, the method according to the invention is additionally carried out at elevated temperature. Preference is given to temperatures from 50° C. to 120° C., more preferably from 60° C. to 100° C., most preferably from 70° C. to 90° C.

In a second embodiment of the invention, the solvent (b3) is a polar aprotic solvent. The solvent (b3) is preferably selected from the group consisting of N,N-disubstituted open-chain and cyclic acid amides, for example dimethylformamide, dimethylacetamide, diethylacetamide, dimethylpropionamide, N-methylpyrrolidone, aliphatic, cycloaliphatic or aromatic nitriles such as acetonitrile, propionitrile or benzonitrile, or linear and cyclic ethers, cyclic lactones and carbonates.

In the context of the invention, the use of the singular such as "a" or "an" or "the" also includes the plural, unless the context clearly indicates otherwise. For example, the term "the solvent" may also cover a multiplicity of solvents, including mixtures thereof, for example a solvent mixture.

In a second embodiment of the invention, small amounts of water are preferably added to the solvent (b3). This is preferably in an amount of 0.1% to 25% by volume, more preferably in an amount of 1-20% by volume, and particularly preferably in an amount of 5-15% by volume. The volume percentages are based here on the solvent (b3).

In a second embodiment of the invention, the presence of the cocatalyst (b5) and the acid (b6) is additionally mandatory in the method according to the invention.

Examples of suitable co-catalysts (b5) are quinones, heteropolyacids and polyoxometalates or metal complexes in which the central metal can easily switch between oxidation states II/III, II/IV, IV/V or I/II through oxidation with oxygen. Central metals of such suitable complexes may be selected, for example, from the group Fe, Cu, Mn, Co, Ni, V. The co-catalysts may also be used in combinations to promote and facilitate the electron transitions during the redox processes. In a preferred embodiment, the co-catalysts are selected from the group consisting of benzoquinones, naphthoquinones, anthraquinones, phosphomolybdic acid, phosphomolybdovanadic acids, phosphomolybdotungstic acids, phosphotungstovanadic acids, phthalocyanine complexes, $FeSO_4$, CuCl, $CuCl_2$, $CuSO_4$, $VOSO_4$.

In a further embodiment of the invention, it is also possible to use other oxidants instead of the cocatalysts for the oxidation of Pd(0) to Pd(II). These are, for example, peroxides and may be selected from the group $H_2O_2$, t-BuOOH, and metal peroxides.

In a second embodiment of the invention, the cocatalyst (b5) is preferably added in a concentration from 1 to 300 mol %, more preferably from 5 to 150 mol %, and most preferably from 21 to 100 mol %. The mol % values are in each case based on the starting material (a).

In a second embodiment of the invention, the acid (b6) is preferably a Brønsted acid and/or a Lewis acid. Suitable Brønsted acids are inorganic mineral acids having weakly coordinating anions and organic carboxylic acids, sulfonic acids, and phosphonic acids. Sulfonic acids are particularly suitable. Lewis acids include compounds having incomplete or unstable electron octets, for example $B(CH_3)_3$, $BF_3$, $AlCl_3$.

In a second embodiment of the invention, the acid (b6) is added preferably in a concentration from 5 to 500 mol %, more preferably from 15 to 300 mol %, even more preferably from 30 to 200 mol %, and most preferably from 50 to 150 mol %. The mol % values are in each case based on the starting material (a).

In a preferred embodiment of the invention, the acid is a Brønsted acid. The Brønsted acid is added preferably in a concentration from 5 to 500 mol %, more preferably from 15 to 300 mol %, even more preferably from 30 to 200 mol %, and most preferably from 50 to 150 mol %. The mol % values are in each case based on the starting material (a).

In a second embodiment of the invention, the palladium (II) salt and/or the palladium(II) complex (b1) is additionally used in a concentration from 0.01 to 20 mol %, more preferably from 0.5 to 10 mol %, and particularly preferably from 1 to 5 mol %. The mol % values are in each case based on the starting material (a).

In a second embodiment of the invention, a palladium compound is formed preferably by mixing a palladium(II) salt and/or a palladium(II) complex (b1) with a Brønsted acid (b6) and a suitable solvent (b3), preferably a polar aprotic solvent. These palladium compounds may occur either in situ or in a separate preparation process ex situ. In the case of separate ex-situ preparation, instead of the palladium(II) salt and/or palladium(II) complex (b) and the acid (b6), preformed palladium compounds are contacted with the starting material (a) and the co-catalyst (b5) and with a suitable solvent (b3) of the preparative method according to the invention.

In a preferred embodiment, this palladium compound is a cationic palladium catalyst.

In a second embodiment of the invention, the palladium compound is used preferably in a concentration from 0.01 mol % to 20 mol %, preferably in a concentration from 0.5 mol % to 10 mol %, and particularly preferably in a concentration from 1 to 5 mol %. The mol % values are in each case based on the starting material (a).

In a second embodiment of the invention, the method according to the invention is preferably carried out at temperatures between 0° C. and 100° C., more preferably between 0° C. and 50° C., and most preferably between 0° C. and 25° C.

INDUSTRIAL APPLICABILITY

According to the present invention, unsaturated macrocyclic monoketones may be prepared, in particular from macrocyclic dienes having a ring size of at least 9 carbon atoms, and very particularly preferably from macrocyclic dienes having a ring size of 16 carbon atoms, which may be further processed, for example into valuable fragrances, flavorings or flavoring agents.

The unsaturated macrocyclic monoketones obtained by the preparative method of the invention may be purified by conventional separation methods, for example by preparative high-performance liquid chromatography (HPLC) or fractional distillation.

EXAMPLES

Examples 1-8

1,9-CHDD (mixture of isomers; 0.120 g, 0.55 mmol) in 2.5 mL of N,N-dimethylacetamide and 0.2 mL of $H_2O$ was added to the glass insert of an autoclave and the calculated amount of the Pd(II) catalyst was added (0.01-20 mol %). The autoclave was flushed with argon and oxygen and then the appropriate oxygen pressure was applied (3 bar). The reaction mixture was then stirred in the autoclave at 90° C.±1° C. for 15 h. On completion of the reaction, the autoclave was cooled and depressurized. The reaction mixture was homogenized by adding THF (tetrahydrofuran). Qualitative analysis of the products was by GC/MS and quantification of the products by the GC-FID method using an internal standard. The results are shown in table 1. X represents the conversion, S the selectivity, and Y the yield.

TABLE 1

Results for examples 1 to 8

| Example | Catalyst | Catalyst [mol %] | $X_{1,9\text{-}CHDD}$ [mol %] | $S_{8\text{-}CHD}$[1] [mol %] | $S_{KETONES}$[1] [mol %] |
|---|---|---|---|---|---|
| 1 | Bis(2,4-pentanedionato)-palladium(II) | 1 | 16 | 39 | 88 |
| | | 3 | 20 | 39 | 86 |
| | | 5 | 27 | 35 | 69 |
| | | 10 | 38 | 33 | 69 |
| | | 20 | 43 | 35 | 69 |
| 2 | Bis(2,2,6,6-tetramethyl-3,5-heptanedionato)palladium(II) | 1 | 12 | 39 | 80 |
| | | 3 | 18 | 42 | 84 |
| | | 5 | 26 | 43 | 84 |
| | | 10 | 40 | 35 | 67 |
| | | 20 | 49 | 42 | 66 |
| 3 | Bis(5,5-dimethyl-2,4-hexanedionato)palladium(II) | 1 | 8 | 50 | 99 |
| | | 3 | 15 | 45 | 84 |
| | | 5 | 16 | 52 | 94 |
| 4 | Bis(6-methyl-2,4-heptanedionato)palladium(II) | 1 | 14 | 35 | 83 |
| | | 3 | 30 | 29 | 69 |
| | | 5 | 45 | 26 | 64 |
| | | 10 | 56 | 24 | 56 |
| 5 | Bis(1,3-diphenylpropane-1,3-dionato)palladium(II) | 1 | 27 | 31 | 74 |
| | | 3 | 43 | 33 | 72 |
| | | 5 | 46 | 31 | 67 |

TABLE 1-continued

Results for examples 1 to 8

| Example | Catalyst | Catalyst [mol %] | $X_{1,9\text{-}CHDD}$ [mol %] | $S_{8\text{-}CHD}$[1] [mol %] | $S_{KETONES}$[1] [mol %] |
|---|---|---|---|---|---|
| 6 | Bis(1-(4-methoxyphenyl)-3-(4-tert-butyl-phenyl)propane-1,3-dionato)palladium(II) | 1<br>3<br>5 | 13<br>31<br>32 | 39<br>37<br>39 | 95<br>80<br>81 |
| 7 | Bis(1,1,1-trifluoro-2,4-pentanedionato)palladium(II) | 0.1<br>0.5<br>1<br>3<br>5<br>10 | 15<br>27<br>54<br>77<br>76<br>76 | 22<br>21<br>18<br>14<br>14<br>20 | 70<br>68<br>59<br>42<br>38<br>41 |
| 8 | Bis(1,1,1,5,5,5-hexafluoro-2,4-pentanedionato)palladium(II) | 0.01<br>0.05<br>0.1<br>0.5<br>1<br>3<br>5<br>10 | 10<br>18<br>23<br>48<br>71<br>73<br>73<br>51 | 28<br>20<br>21<br>19<br>13<br>11<br>12<br>13 | 66<br>65<br>65<br>60<br>45<br>37<br>32<br>40 |

[1]based on $X_{1,9\text{-}CHDD}$

Example 9-13:
Bis(2,4-pentanedionato)palladium(II) and Various Solvents 1,9-CHDD (mixture of isomers; 0.120 g, 0.55 mmol) in 2.5 mL of solvent (N,N-dimethylformamide, N,N-dimethylacetamide, N,N-dimethylpropionamide or N-methyl-2-pyrrolidone) and 0.2 mL of $H_2O$ was added to the glass insert of an autoclave and bis(2,4-pentanedionato)palladium(II) (3 mol %) was added. The autoclave was flushed with argon and oxygen and then the appropriate oxygen pressure was applied (3 bar). The reaction mixture was then stirred in the autoclave at 90° C.±1° C. for 15 h. On completion of the reaction, the autoclave was cooled and depressurized. The reaction mixture was homogenized by adding THF. Qualitative analysis of the products was by GC/MS and quantification of the products by the GC-FID method using an internal standard. The results are shown in table 2.

TABLE 2

Results for examples 9 to 13

| Example | Solvent | Time [h] | $X_{1,9\text{-}CHDD}$ [mol %] | $S_{8\text{-}CHD}$[1] [mol %] | $S_{KETONES}$[1] [mol %] |
|---|---|---|---|---|---|
| 9 | N,N-Dimethylformamide | 15 | 0 | 0 | 0 |
| 10 | N,N-Dimethylacetamide | 15 | 20 | 39 | 86 |
| 11 | N,N-Dimethylpropionamide | 15 | 9 | 17 | 33 |
| 12 | N-Methyl-2-pyrrolidone | 15 | 61 | 22 | 59 |
| 13 | N-Methyl-2-pyrrolidone | 5 | 11 | 39 | 94 |

[1]based on $X_{1,9\text{-}CHDD}$

Examples 14 to 16:
Bis(2,4-pentanedionato)palladium(II) and Co-Catalysts 1,9-CHDD (mixture of isomers; 0.120 g, 0.55 mmol) in 2.5 mL of N,N-dimethylacetamide and 0.2 mL of $H_2O$ was added to the glass insert of an autoclave and bis(2,4-pentanedionato)palladium(II) (1 mol %) and the relevant amount of a co-catalyst was added. The autoclave was flushed with argon and oxygen and then the appropriate oxygen pressure was applied (3 bar). The reaction mixture was then stirred in the autoclave at 90° C.±1° C. for 15 h. On completion of the reaction, the autoclave was cooled and depressurized. The reaction mixture was homogenized by adding THF. Qualitative analysis of the products was by GC/MS and quantification of the products by the GC-FID method using an internal standard. The results are shown in table 3.

TABLE 3

Results for examples 14 to 16

| Example | Solvent | Co-cat. [mol %] | $X_{1,9\text{-}CHDD}$ [mol %] | $S_{8\text{-}CHD}$[1] [mol %] | $S_{KETONES}$[1] [mol %] |
|---|---|---|---|---|---|
| 14 | $CuCl_2$ | 2 | 0 | 0 | 0 |
| 15 | Cu(acetylacetonate)$_2$ | 2 | 11 | 27 | 80 |
| 16 | Benzoquinone | 100 | 0 | 0 | 0 |

[1]based on $X_{1,9\text{-}CHDD}$

Examples 17-27: Pd(OAc)$_2$ or Pd(NO$_3$)$_2$·2H$_2$O and Various Solvent Ratios In a closable 4 ml glass reactor with screw cap and septum, a solvent system consisting of N,N-dimethylacetamide, acetonitrile, and water (Vtot.=3.06 ml) is charged with 1,9-CHDD (mixture of isomers; 44 mg; 0.2 mmol). To this solution are added the palladium(II) precursor (0.01 mmol; 5.0 mol %), benzoquinone (22 mg; 0.2 mmol), and aqueous tetrafluoroboric acid (50% by weight; 125 µl; 0.83 mmol). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 4.

TABLE 4

Results for examples 17-27

| Example | Palladium(II) precursor | Solvent ratio (DMA/MeCN/$H_2O$) [% by volume] | $X_{1,9\text{-}CHDD}$ [mol %] | $S_{8\text{-}CHD}$[1] [mol %] | $S_{DIKETONE}$[1] [mol %] | $Y_{8\text{-}CHD}$[1] [mol %] |
|---|---|---|---|---|---|---|
| 17 | Palladium(II) acetate | 0/7/1 | 26 | 53 | 5 | 14 |
| 18 | Palladium(II) acetate | 1/6/1 | 26 | 73 | 8 | 19 |
| 19 | Palladium(II) acetate | 2/5/1 | 32 | 76 | 8 | 25 |
| 20 | Palladium(II) acetate | 3/4/1 | 39 | 67 | 11 | 26 |
| 21 | Palladium(II) acetate | 4/3/1 | 40 | 72 | 9 | 29 |
| 22 | Palladium(II) acetate | 5/2/1 | 46 | 67 | 12 | 31 |
| 23 | Palladium(II) acetate | 6/1/1 | 44 | 63 | 7 | 28 |
| 24 | Palladium(II) nitrate dihydrate | 4/3/0 | 31 | 84 | 2 | 26 |
| 25 | Palladium(II) nitrate dihydrate | 8/6/1 | 42 | 81 | 5 | 34 |
| 26 | Palladium(II) nitrate dihydrate | 4/3/1 | 45 | 79 | 8 | 35 |
| 27 | Palladium(II) nitrate dihydrate | 4/3/2 | 34 | 62 | 13 | 21 |

[1]based on $X_{1,9\text{-}CHDD}$

Examples 28 to 34: Dimethylacetamide (DMA)/MeCN/$H_2O$=4/3/1 and Variation of the Palladium(II) Precursor In a closable 4 ml glass reactor with screw cap and septum, a solvent system consisting of N,N-dimethylacetamide, acetonitrile, and water (DMA/MeCN/$H_2O$=4/3/1; Vtot.=3.06 ml) is charged with 1,9-CHDD (mixture of isomers; 44 mg; 0.2 mmol). To this solution are added the palladium(II) precursor (0.01 mmol; 5.0 mol %), benzoquinone (22 mg; 0.2 mmol), and aqueous tetrafluoroboric acid (50% by weight; 125 µl; 0.83 mmol). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 5.

TABLE 5

Results for examples 28-34

| Example | Palladium(II) precursor | $X_{1,9\text{-}CHDD}$ [mol %] | $S_{8\text{-}CHD}$[1] [mol %] | $S_{DIKETONE}$[1] [mol %] | $Y_{8\text{-}CHD}$[1] [mol %] |
|---|---|---|---|---|---|
| 28 | Palladium(II) sulfate dihydrate | 41 | 76 | 6 | 31 |
| 29 | Bis(2,2,6,6-tetramethyl-3,5-heptanedionato) palladium(II) | 9 | 75 | 0 | 7 |
| 30 | Palladium(II) nitrate dihydrate | 45 | 79 | 8 | 35 |
| 31 | Bis(triphenylphosphine)-palladium(II) dichloride | 0 | 0 | 0 | 0 |
| 32 | Bis(acetonitrile)dichloropalladium | 3 | 87 | 0 | 3 |
| 33 | Palladium(II) chloride | 5 | 64 | 0 | 3 |
| 34 | Palladium(II) acetate | 43 | 72 | 8 | 31 |

[1]based on $X_{1,9\text{-}CHDD}$

Examples 35 to 41: DMA/MeCN/$H_2O$=4/3/1 and Variation of the Amount of $Pd(NO_3)_2 \cdot 2H_2O$ Catalyst In a closable 4 ml glass reactor with screw cap and septum, a solvent system consisting of N,N-dimethylacetamide, acetonitrile, and water (DMA/MeCN/$H_2O$=4/3/1; Vtot.=3.06 ml) is charged with 1,9-CHDD (mixture of isomers; 44 mg; 0.2 mmol). To this solution are added palladium(II) nitrate dihydrate (0.01-20 mol %), benzoquinone (22 mg; 0.2 mmol), and aqueous tetrafluoroboric acid (50% by weight; 125 µl; 0.83 mmol). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 6.

TABLE 6

Results for examples 35-41

| Example | Pd(NO$_3$)$_2$ amount [mol %] | X$_{1,9\text{-}CHDD}$ [mol %] | S$_{8\text{-}CHD}$[1] [mol %] | S$_{DIKETONE}$[1] [mol %] | Y$_{8\text{-}CHD}$[1] [mol %] |
|---|---|---|---|---|---|
| 35 | 0.1 | 3 | 15 | 0 | 0 |
| 36 | 0.5 | 7 | 51 | 0 | 3 |
| 37 | 1.0 | 10 | 67 | 0 | 7 |
| 38 | 2.5 | 21 | 81 | 2 | 17 |
| 39 | 5.0 | 45 | 79 | 8 | 35 |
| 40 | 10.0 | 42 | 64 | 6 | 27 |
| 41 | 20.0 | 52 | 51 | 5 | 27 |

[1]based on X$_{1,9\text{-}CHDD}$

Examples 42 to 48: DMA/MeCN/H$_2$O=4/3/1; Pd(NO$_3$)$_2$.2H$_2$O and Variation of the Reaction Temperature In a 25 ml round-bottomed flask, a solvent system consisting of N,N-dimethylacetamide, acetonitrile, and water (DMA/MeCN/H$_2$O=4/3/1; Vtot.=15.3 ml) is charged with 1,9-CHDD (mixture of isomers; 220 mg; 1 mmol). To this solution are added palladium(II) nitrate dihydrate (0.05 mmol; 5.0 mol %), benzoquinone (108 mg; 1 mmol), and aqueous tetrafluoroboric acid (50% by weight; 625 µl; 4.15 mmol). The reactor is closed with a stopper and the reaction solution is stirred vigorously for 20 hours in a temperature range of 0-80° C. The reactor is then warmed/cooled and the reaction mixture diluted to constant volume with tetrahydrofuran and homogenized. Qualitative and quantitative analysis of the reaction products is carried out in a GC/MS with FID on the basis of an internal standard (n-hexadecane). The results are shown in table 7.

TABLE 7

Results for examples 42-48

| Example | Temperature [° C.] | X$_{1,9\text{-}CHDD}$ [mol %] | S$_{8\text{-}CHD}$[1] [mol %] | S$_{DIKETONE}$[1] [mol %] | Y$_{8\text{-}CHD}$[1] [mol %] |
|---|---|---|---|---|---|
| 42 | 0 | 29 | 88 | 3 | 25 |
| 43 | 25 | 39 | 79 | 8 | 31 |
| 44 | 40 | 37 | 82 | 5 | 30 |
| 45 | 50 | 34 | 81 | 3 | 27 |
| 46 | 60 | 32 | 82 | 3 | 26 |
| 47 | 70 | 32 | 76 | 2 | 25 |
| 48 | 80 | 31 | 67 | 2 | 21 |

[1]based on X$_{1,9\text{-}CHDD}$

Examples 49 to 54: DMA/MeCN/H$_2$O=8/6/1; Pd(NO$_3$)$_2$.2H$_2$O and Variation of the Brønsted Acid or of an Acid Anion In a closable 4 ml glass reactor with screw cap and septum, a solvent system consisting of N,N-dimethylacetamide, acetonitrile, and water (DMA/MeCN/H$_2$O=8/6/1; Vtot.=3.06 ml) is charged with 1,9-CHDD (mixture of isomers; 44 mg; 0.2 mmol). To this solution are added palladium(II) nitrate dihydrate (0.01 mol %; 5.0 mol %), benzoquinone (22 mg; 0.2 mmol), and an acid or an acid anion in the form of a silver salt (0.83 mmol). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 8.

TABLE 8

Results for examples 49-54

| Example | Acid/Silver salt | X$_{1,9\text{-}CHDD}$ [mol %] | S$_{8\text{-}CHD}$[1] [mol %] | S$_{DIKETONE}$[1] [mol %] | Y$_{8\text{-}CHD}$[1] [mol %] |
|---|---|---|---|---|---|
| 49 | Tetrafluoroboric acid | 42 | 81 | 5 | 34 |
| 50 | Methanesulfonic acid | 51 | 75 | 9 | 38 |
| 51 | Perchloric acid | 49 | 67 | 4 | 33 |
| 52 | para-Toluenesulfonic acid | 54 | 76 | 7 | 41 |
| 53 | Silver trifluoromethanesulfonate | 17 | 54 | 0 | 9 |
| 54 | Aquivion ® | 1 | 0 | 0 | 0 |

[1]based on X$_{1,9\text{-}CHDD}$

Examples 55 to 63: DMA/MeCN/H$_2$O=8/6/1; Pd(NO$_3$)$_2$.2H$_2$O and Variation of the p-TsOH Concentration In a closable 4 ml glass reactor with screw cap and septum, a solvent system consisting of N,N-dimethylacetamide, acetonitrile, and water (DMA/MeCN/H$_2$O=8/6/1; Vtot.=3.06 ml is charged with 1,9-CHDD (mixture of isomers; 44 mg; 0.2 mmol). To this solution are added palladium(II) nitrate dihydrate (0.01 mmol; 5.0 mol %), benzoquinone (22 mg; 0.2 mmol), and para-toluenesulfonic acid monohydrate (5-430 mol %). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 9.

TABLE 9

Results for examples 55-63

| Example | Acid concentration [mol %] | X$_{1,9\text{-}CHDD}$ [mol %] | S$_{8\text{-}CHD}$[1] [mol %] | S$_{DIKETONE}$[1] [mol %] | Y$_{8\text{-}CHD}$[1] [mol %] |
|---|---|---|---|---|---|
| 55 | 5 | 18 | 60 | 0 | 11 |
| 56 | 12.5 | 22 | 66 | 0 | 15 |
| 57 | 50 | 41 | 74 | 4 | 30 |
| 58 | 100 | 45 | 75 | 5 | 34 |
| 59 | 125 | 47 | 79 | 5 | 37 |
| 60 | 150 | 47 | 74 | 5 | 35 |
| 61 | 175 | 52 | 74 | 6 | 39 |
| 62 | 200 | 54 | 76 | 8 | 41 |
| 63 | 415 | 53 | 78 | 7 | 41 |

[1]based on X$_{1,9\text{-}CHDD}$

Examples 64 to 69: DMA/MeCN/H$_2$O=8/6/1; 125 Mol % p-TsOH and Variation of the Amount of Pd(NO$_3$)$_2$.2H$_2$O Catalyst In a closable 4 ml glass reactor with screw cap and septum, a solvent system consisting of N,N-dimethylacetamide, acetonitrile, and water (DMA/MeCN/H$_2$O=8/6/1; Vtot.=3.06 ml) is charged with 1,9-CHDD (mixture of isomers; 44 mg; 0.2 mmol). To this solution are added palladium(II) nitrate dihydrate (0.01-10 mol %), benzoquinone (22 mg; 0.2 mmol), and para-toluenesulfonic acid monohydrate (48 mg; 0.25 mmol). The reactor is closed, the septum is pierced with a disposable needle, and the reaction solution is stirred vigorously for 20 hours at room temperature. The reaction solution is then diluted to constant volume with tetrahydrofuran and homogenized. Qualitative and quantitative analysis of the reaction products is carried out in a GC/MS with FID on the basis of an internal standard (n-hexadecane). The results are shown in table 10.

TABLE 10

Results for examples 64-69

| Example | Pd(NO$_3$)$_2$ amount [mol %] | X$_{1,9\text{-}CHDD}$ [mol %] | S$_{8\text{-}CHD}$[1] [mol %] | S$_{DIKETONE}$[1] [mol %] | Y$_{8\text{-}CHD}$[1] [mol %] |
|---|---|---|---|---|---|
| 64 | 0.1 | 2 | 42 | 0 | 1 |
| 65 | 0.5 | 6 | 75 | 0 | 5 |
| 66 | 1.0 | 12 | 76 | 0 | 10 |
| 67 | 2.5 | 27 | 81 | 2 | 22 |
| 68 | 5.0 | 47 | 79 | 5 | 37 |
| 69 | 10.0 | 68 | 68 | 11 | 46 |

[1]based on X$_{1,9\text{-}CHDD}$

The invention claimed is:
1. A method for preparing unsaturated macrocyclic monoketones comprising the following steps
   (a) providing macrocyclic dienes having a ring size of at least 9 carbon atoms;
   (b) contacting the starting materials from step (a) with
      (b1) a palladium(II) salt and/or a palladium(II) complex; and
      (b2) a bidenate ligand which contains N,N, N,O, N,S, or O,O donor atoms,
      (b3) an oxidant; and
      (b4) a solvent; and optionally
      (b5) a cocatalyst; and optionally
      (b6) an acid.
2. The method as claimed in claim 1, wherein the solvent (b4) is a polar aprotic solvent and selected from the group consisting of N,N-disubstituted open-chain and cyclic acid amides, aliphatic, cycloaliphatic or aromatic nitriles, linear and cyclic ethers, cyclic carbonates, lactones, and mixtures thereof.
3. The method as claimed in claim 1, wherein the palladium(II) salt and/or the palladium(II) complex (b1) are selected from the group consisting of palladium chloride, palladium bromide, H2PdCl4, Li2PdCl4, Na2PdCl4, K2PdCl4, (NH4)2PdCl4, palladium acetate, palladium trifluoroacetate, palladium benzoate, palladium nitrate, palladium sulfate tetrakis(acetonitrile)palladium(II) tetrafluoroborate, tetrakis(acetonitrile)palladium(II) bis(trifluoromethanesulfonate), and mixtures thereof.
4. The method as claimed in claim 1, wherein the palladium(II) salt and/or the palladium(II) complex (b1) form with the bidentate ligand (b4) a palladium compound of the formula (I) and/or of the formula (II)

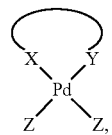

I where X and Y each independently represent N,N, O,N or O,O; and
where Z each independently represent a halogen, acetate, trimethylacetate, trifluoromethylacetate, MeCN, PhCN, NO2, NO, nitrate, nitrite or sulfate;

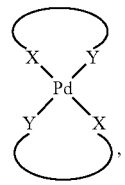

II where X and Y each independently represent O,O, N,N or O,N.
5. The method as claimed in claim 4, wherein the palladium compound is added in a concentration from 0.01 to 25 mol % based on the starting material (a).
6. The method as claimed in claim 1, wherein an oxygen-containing gas is used as the oxidant (b3).
7. The method as claimed in claim 6, wherein the oxygen-containing gas contains oxygen in a concentration from 1% to 100% by volume.
8. The method as claimed in claim 1, wherein the method is carried out at temperatures from 50° C. to 120° C.
9. The method as claimed in claim 1, wherein the co-catalyst (b5) and the acid (b6) are mandatory.
10. The method as claimed in claim 9, wherein the co-catalyst (b5) is selected from the group consisting of benzoquinones, naphthoquinones, anthraquinones, phosphomolybdic acid, phosphomolybdovanadic acids, phosphomolybdotungstic acids, phosphotungstovanadic acids, phthalocyanine complexes, FeSO4, CuCl, CuCl2, CuSO4, VOSO4, and mixtures thereof, and the acid (b6) is a Brønsted acid or Lewis acid.
11. The method as claimed in claim 10, wherein the co-catalyst (b5) is added in a concentration from 1 to 300 mol %, based on the starting material (a).
12. The method as claimed in claim 10, wherein the acid (b6) is added in a concentration from 5 to 500 mol % based on the starting material (a).
13. The method as claimed in claim 9, wherein the palladium(II) salt and/or the palladium(II) complex (b1) is added in a concentration from 0.01 to 20 mol %, preferably from 0.5 to 10 mol %, and more preferably from 1 to 5 mol %, in each case based on the starting material (a).
14. The method as claimed in claim 10, wherein the method is carried out at temperatures between 0° C.
15. The method of claim 1, wherein the macrocyclic diene (a) has a ring size of from 12 to 30 carbon atoms.
16. The method of claim 1, wherein the macrocyclic diene (a) has a ring size of from 12 to 18 carbon atoms.

* * * * *